(12) United States Patent
Bandiera et al.

(10) Patent No.: US 6,268,362 B1
(45) Date of Patent: Jul. 31, 2001

(54) AMINO ANTHRACYCLINONE DERIVATIVES AND THEIR USE IN THE TREATMENT OF AMYLOIDOSIS

(75) Inventors: Tiziano Bandiera, Gambolò ; Daniele Fancelli, Milan; Mario Varasi, Milan; Michele Caruso, Milan; Jacqueline Lansen, San Vittore Olona; Antonino Suarato, Milan, all of (IT)

(73) Assignee: Pharmacia & Upjohn SpA, Milan (IT)

( * ) Notice: Subject to any disclaimer, the term of this patent is extended or adjusted under 35 U.S.C. 154(b) by 0 days.

(21) Appl. No.: 09/622,921

(22) PCT Filed: Feb. 25, 1999

(86) PCT No.: PCT/EP99/01300

§ 371 Date: Sep. 7, 2000

§ 102(e) Date: Sep. 7, 2000

(87) PCT Pub. No.: WO99/46254

PCT Pub. Date: Sep. 16, 1999

(30) Foreign Application Priority Data

Mar. 10, 1998 (GB) .................................................. 9805080

(51) Int. Cl.[7] ...................... A61K 31/5377; A61F 25/88; C07D 413/02
(52) U.S. Cl. .................... 514/235.5; 544/131; 546/15; 546/285
(58) Field of Search ........................... 544/131; 546/285; 514/235.3

(56) References Cited

U.S. PATENT DOCUMENTS

| | | |
|---|---|---|
| 5,637,572 | 6/1997 | Merlini et al. . |
| 5,731,313 | 3/1998 | Suarato et al. . |
| 5,985,887 | 11/1999 | Caruso et al. . |
| 5,998,615 | 12/1999 | Suarato et al. . |
| 6,096,888 | 8/2000 | Surato et al. . |
| 6,103,700 | 8/2000 | Bandiera et al. . |

OTHER PUBLICATIONS

Suavato et al, WO 96/04895, (Feb. 1996).

*Primary Examiner*—Robert W. Ramsuer
(74) *Attorney, Agent, or Firm*—Oblon, Spivak, McClelland, Maier & Neustadt, P.C.

(57) ABSTRACT

A compound of formula (1), wherein $R_1$ represents hydrogen, hydroxy, a group of formula $OR_7$, wherein $R_7$ is $C_1$–$C_6$ alkyl, $C_2$–$C_6$ alkenyl; $R_2$ represents hydrogen, hydroxy, diethylamino, piperidino, tetrahydropyridino or morpholino, and either $R_3$, taken alone, represtnts hydrogen or hydroxy, and $R_4$ and $R_5$, taken alone, independently represent hydrogen, hydroxy or, taken together with the carbon atom, represent a carbonyl group; or $R_3$ and $R_4$, taken together, represent a group of formula (A), wherein $R_8$ and $R_9$ represent a $C_1$–$C_6$ alkyl and $R_5$ represents hydrogen; $R_6$ represents hydrogen or a phenyl group, optionally substituted by methyl, methoxy or halogen and the pharnaceutically acceptable salt thereof, is useful in the treatment of amyloidosis. Processes for the preparation and pharmaceutical compositions are also described.

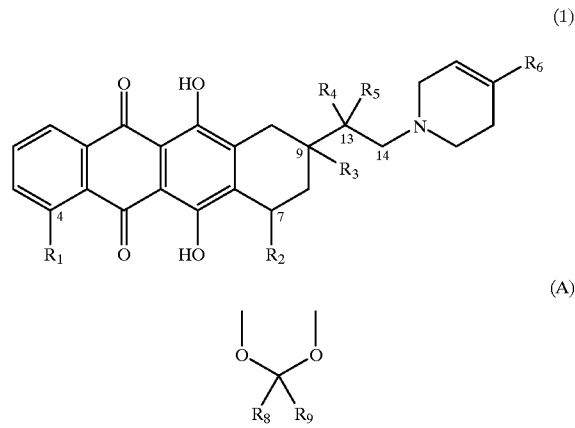

8 Claims, No Drawings

AMINO ANTHRACYCLINONE DERIVATIVES AND THEIR USE IN THE TREATMENT OF AMYLOIDOSIS

This application is a National Stage Application of International Application Ser. No. PCT/EP99/01300, filed Feb. 25, 1999, which claims priority GB 9805080.0, filed Mar. 10, 1998.

The present invention relates to anthracyclinone derivatives, to their use for the treatment of amyloidoses, to the methods for their preparation and to the pharmaceutical compositions containing them.

Our previous PCT Patent Application WO 96/04895 provides the new use of anthracyclinone derivatives in the treatment of amyloidosis, some novel compounds, processes for their preparation and pharmaceutical compositions containing them.

Unexpectedly, we found that the presence of a particular heterocyclic residue on the anthracyclinone skeleton is associated with a better activity of this class of compounds as inhibitors of the aggregation process of amyloidogenic peptides.

The present invention provides anthracyclinone derivatives of formula 1

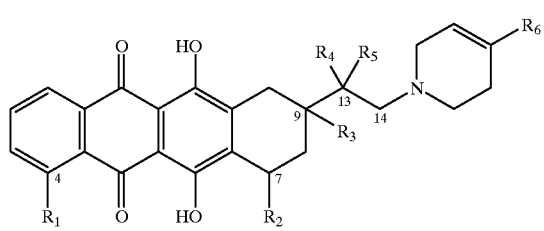

wherein $R_1$ represents:
  hydrogen,
  hydroxy,
  a group of formula $OR_7$ wherein $R_7$ is $C_1$–$C_6$ alkyl, $C_2$–$C_6$ alkenyl;
$R_2$ represents:
  hydrogen,
  hydroxy,
  diethylamino, piperidino, tetrahydropyridino or morpholino;
  either $R_3$, taken alone, represents hydrogen or hydroxy; and $R_4$ and $R_5$, taken alone, independently represent hydrogen, hydroxy or, taken together with the carbon atom, represent a carbonyl group;
  or $R_3$ and $R_4$, taken together, represent a group of formula

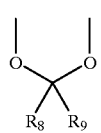

wherein $R_8$ and $R_9$ represent a $C_1$–$C_6$ alkyl, and $R_5$ represents hydrogen;
$R_6$ represents:
  hydrogen or
  a phenyl group, optionally substituted by methyl, methoxy or halogen, and the pharmaceutically acceptable salt thereof Preferred compounds of formula 1 are those wherein:
$R_1$ represents:
  hydrogen,
  hydroxy or
  methoxy;
$R_2$ represents:
  hydrogen,
  hydroxy or
  morpholino
$R_3$ represents hydroxy;
$R_4$, taken alone, represents hydroxy;
$R_5$, taken alone, represents hydrogen or
$R_4$ and $R_5$ taken together with the carbon atom represent a carbonyl group;
$R_6$ represents hydrogen, and the pharmaceutically acceptable salt thereof.

The term $C_1$–$C_6$ "alkyl" as used herein includes both straight and branched chain alkyl groups or moieties such as methyl, ethyl, propyl, isopropyl, butyl, isobutyl, t-butyl, pentyl, hexyl and, in case of pentyl and hexyl, a branched chain isomer thereof.

The term $C_2$–$C_6$ "alkenyl" as used herein includes both straight and branched chain radicals of up to 6 carbons such as, for example, vinyl, allyl, butenyl, pentenyl and hexenyl.

The term "halogen" as used herein means fluorine, chlorine, bromine or iodine.

This invention also includes all the possible isomers of compounds of formula 1 and mixtures thereof, for example diastereoisomeric mixtures and racemic mixtures. Thus, the stereocenter at position 9, and the possible stereocenters at positions 7 and 13, may have the (R) configuration or the (S) configuration or both, ie. a mixture of stereoisomers is present.

The present invention also provides the salts of compounds of formula 1. The salts are, typically, physiologically tolerable or pharmaceutically acceptable salts formed with suitable inorganic or organic acids. Examples of inorganic acids are, for instance, hydrochloric and sulfuric acid, while organic acids may be mono-, di- and tricarboxylic acids, like, for examples, acetic, trifluoroacetic, tartaric or citric acid, and sulfonic acids like, for example, methanesulfonic or ptoluensulphonic acid.

Compounds of formula 1, wherein $R_3$, $R_3$, $R_4$, $R_5$ and $R_6$ are as defined above and $R_2$ is hydrogen or hydroxy, can be prepared by the following procedures:

(a) reacting a compound of formula 2,

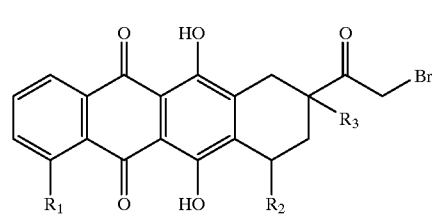

wherein $R_1$, and $R_3$ are as defined above and $R_2$ is hydrogen or hydroxy, with acompound of formula 3

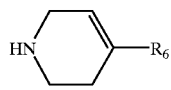

3

(b) converting a compound of formula 1 as defined above into a different compound of formula 1 by appropriate chemical reactions, such as reduction, substitution or condensation.

Compounds of formula 1 obtained according to procedures a) or b) can be transformed into pharmaceutically acceptable salts thereof.

A compound of formula 1, wherein $R_1$, $R_3$ and $R_6$ are as defined above, $R_2$ is hydrogen or hydroxy and $R_4$ and $R_5$ taken together represent a carbonyl group, is obtained according to procedure a) by reacting a compound of formula 2 with a compound of formula 3 in a proper organic solvent like dichloromethane, chloroform, acetone, dioxane or dimethylformamide at a temperature ranging from −10° C. to room temperature and for a period of from 6 to 48 hours. An organic base such as diethylamine or ethyldiisopropylamine may be present. Preferred reaction conditions encompass the use of equimolar amounts of compound 2 and 3 and ethyldiisopropylamine in dichloromethane at room temperature for a period of 6 to 24 hours.

Compounds of formula 2, wherein $R_1$ and $R_3$ are as defined above and $R_2$ is hydrogen or hydroxy, can be prepared by bromination of a compound of formula 4,

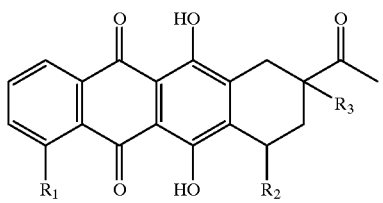

4 wherein $R_1$ and $R_3$ are as defined above and $R_2$ is hydrogen or hydroxy, in analogy to known procedures reported in the literature (see, for instance, T. H. Smith et al., *J. Org. Chem.* 1977, vol. 42, p. 3653).

Compounds of formula 4, wherein $R_1$ and $R_3$ are as defined above and $R_2$ is hydrogen or hydroxy, may be prepared, depending on the nature of the substituents, starting from known anthracyclinones by appropriate chemical modifications (see: F. Arcamone in *Doxorubicin Anticancer Antibiotics, Medicinal Chemistry,* a series of monographs, vol. 17, Academic Press, 1981).

According to procedure b), a compound of formula 1 as defined above, may be converted into a different compound of formula 1 by appropriate synthetic procedures described for the anthracyclines or anthracyclinones (see: F. Arcamone in *Doxorubicin Anticancer Antibiotics,* Medicinal Chemistry, a series of monographs, vol. 17, Academic Press, 1981) or by general synthetic procedures (see: J. March, *Advanced Organic Chemistry,* IV Ed., J. Wiley & Sons, 1992).

As an example, a compound of formula 1, wherein $R_1$, $R_2$, $R_3$ and $R_6$ are as defined above and $R_4$ and $R_5$ taken together represent a carbonyl group can be converted into a compound of formula 1, wherein $R_1$, $R_2$, $R_3$ and $R_6$ are as defined above, $R_4$ represents hydroxy and R. represents hydrogen by reduction with sodium borohydride or sodium cyanoborohydride.

In another example, a compound of formula 1, wherein $R_1$, $R_3$ and $R_6$ are as defined above, and
either $R_2$ represents hydroxy and $R_4$ and $R_5$ are taken together represent a carbonyl group,
or $R_2$ and $R_4$ represent hydroxy and $R_5$ represents hydrogen, can be converted into a compound of formula 1, wherein $R_1$, $R_3$ and $R_6$ are as defined above, and
either $R_2$ represents hydrogen and $R_4$ and $R_5$ taken together represent a carbonyl group,
or $R_4$ represents hydroxy and $R_2$ and $R_5$ represent hydrogen, by treatment with sodium dithionite.

In another example, a compound of formula 1, wherein $R_1$ and $R_6$ are as defined above, $R_2$ and $R_5$ represent hydrogen and $R_3$ and $R_4$ represent hydroxy, can be converted into a compound of formula 1, wherein $R_1$ and $R_6$ are as defined above, $R_2$ and $R_5$ represent hydrogen, $R_3$ and $R_4$ taken together represent a group of formula

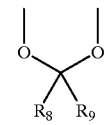

wherein $R_8$ and $R_9$ are as above defined, by condensation with a compound of the formula $R_8COR_9$ or $R_8C(OCH_3)_2OR_9$ wherein $R_8$ and $R_9$ are as above defined, for example acetone or 2,2-dimethoxy propane, in the presence of an acid catalyst.

In a further example, a compound of formula 1, wherein $R_1$, $R_3$ and $R_6$ are as defined above, $R_4$ and $R_5$ are taken together to represent a carbonyl group and $R_2$ represents diethylamino, piperidino, tetrahydropyridino or morpholino, can be prepared by reacting a compound of formula 1, wherein $R_1$, $R_3$ and $R_6$ are as defined above, $R_2$ represents hydroxy, $R_4$ and $R_5$ taken together represent a carbonyl group, by reaction with ethylchlorocarbonate to give an intermediate compound of formula 5,

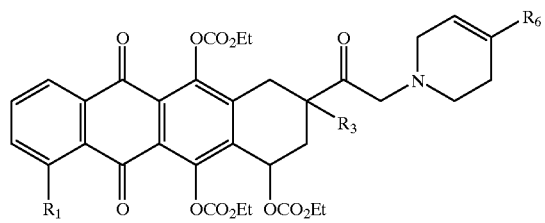

5 wherein $R_1$, $R_3$ and $R_6$ are as defined above in analogy to a procedure described in the literature (see: L. Bernardi et al. *Il Farmaco Ed. Sc.* 1979, vol. 34, p. 884), followed by substitution with excess diethylamine, piperidine, tetrahydropyridine or morpholine.

Compounds of formula 1 obtained according to procedures a) or b) can be transformed into pharmaceutically acceptable salts thereof by dissolving the free base in a proper organic solvent like dichloromethane, methanol, ethanol or dioxane and adding a solution of a pharmaceutically acceptable inorganic or organic acid in methanol, ethanol or dioxane. The resulting salt of compound 1 is obtained by evaporation or concentration of the salt solution or the salt is precipitated by addition of diethyl ether to the salt solution.

The compounds of the present invention can be used in the treatment of amyloidoses as they are characterized by high inhibitory activity on the formation of amyloid deposits by amyloidogenic proteins and are able to induce the degradation of existing amyloid deposits.

The term amyloidoses indicates a group of diseases whose common characteristic is the presence, in the extracellular space, of amyloid deposits. Amyloidogenic proteins are proteins that have the tendency to aggregate and precipitate as amyloid. Proteins that precipitate as amyloid are both normal proteins, or truncated forms thereof, and mutated proteins, where one or more of the amino acid residues occurring at certain positions of the normal protein sequence are replaced by a different amino acid. Amyloid deposits are composed of insoluble fibrils, also referred to as amyloid fibrils. Amyloid fibrils cause cellular degeneration and organ failure that, in turn, result in different pathologies depending on the tissues and organs involved.

The basis for the activity of the compounds of the present invention in different types of amyloidosis is to be found in the common ultrastructural organization of amyloid fibrils despite the fact that they can he formed from a variety of widely differing proteins (see: Glenner G. G., New Ehgland J. Med. 1980, vol 302, p. 1283 and p. 1333).

The compounds of the present invention are characterized by an acceptable toxicity and can be used to make medicaments useful to prevent, to arrest or to slow down the formation of or to induce the degradation of amyloid deposits that are formed by different amyloidogenic proteins Therefore, the compounds of the present invention can be used in the prevention and in the treatment of different types of amyloidotic diseases such as systemic amyloidoses and amyloidoses of the peripheral and central nervous system. Amyloidoses of the central nervous system include, for example, Alzheimer's disease, Down Syndrome, spongiform encephalopathies such as Creutzfeld-Jacob disease and the like.

In the case of Alzheimer's disease, the protein that is found in amyloid deposits is referred to as amyloid β-protein or β-amyloid protein and is generally indicated as Aβ protein. The term Aβ protein encompasses proteins of different length. In brain amyloid deposits, Aβ proteins composed of 39 to 43 amino acids are usually found. Neurodegenerative disorders such as spongiform encephalopathies are characterized by the extracellular deposition of amyloid originated from a protein referred to as prion protein (PrP).

The compounds disclosed in the present invention interfere with the aggregation of monomeric Aβ1-40 peptide stimulated by a seed of Aβ1-40 amyloid fibrils. The activity of the compounds was assessed according to the procedure reported below.

An Aβ1-40 peptide monomer stock solution was prepared by dissolving the peptide in dimethylsulfoxide at a concentration of 33.33 mg/ml. The stock solution was further diluted 11.5 times with dimethylsulfoxide. This solution was then diluted with 10 mM phosphate buffer pH 7.4 containing 150 mM sodium chloride to prepare the test solution. To an eppendorf tube containing 47 $\mu$l of Aβ1-40 peptide monomer solution were added 3 $\mu$l of a 830 $\mu$M water solution of the test compound containing 66.4 $\mu$M, based on the Aβ1-40 monomer content, of pre-formed sonicated Aβ1-40 fibrils: the resulting solution was 20 $\mu$M in Aβ1-40 monomer, 50 $\mu$M in the test compound and contained 4 $\mu$M, based on the Aβ1-40 monomer content, of pre-formed sonicated Aβ1-40 fibrils. The aggregation was allowed to proceed for two hours at 37° C. The suspension was then centrifuged at 15000 rpm for 15 minutes at +4° C., the supernatant was collected and the Aβ1-40 monomer was quantitated by HPLC. The activity of some representative compounds is reported in Table 1. The activity is expressed as the percent of inhibition of the aggregation of a 20 $\mu$M Aβ1-40 monomer solution stimulated by 4 $\mu$M, based on the Aβ1-40 monomer content, pre-formed sonicated Aβ1-40 fibrils.

TABLE 1

| Compound | % inhibition |
| --- | --- |
| 1a | 74.1 |
| 1d | 47.3 |
| 1k | 52.1 |
| A17 | 11.4 |

As shown in the above table, the compounds of formula 1 of the present invention are characterized by a better activity than the compounds disclosed in our previous PCT Patent Application WO 96/04895. As reference, we have tested the compound A17 of our PCT Patent Application WO 96/04895 (7-deoxy-14-(4-morpholinyl)-daunomycinone), which displays only a 11.4% inhibition.

The present invention provides a pharmaceutical composition comprising a compound of formula 1 or a pharmaceutically acceptable salt thereof, as active ingredient, in association with a pharmaceutically acceptable carrier, excipient or other additive, if necessary.

Also provided is a compound of formula 1, as defined above, or a pharmaceutically acceptable salt thereof, for use in the treatment of the human or animal body. Moreover, the present invention provides the use of a compound of formula 1, or a pharmaceutically acceptable salt thereof, in the manufacture of a medicament for use in the treatment of an amyloidotic disease.

The pharmaceutical compositions containing a compound of formula 1 or salts thereof may be prepared in a conventional way by employing conventional non-toxic pharmaceutical carriers or diluents in a variety of dosage forms and ways of administration.

In particular, the compounds of the formula 1 can be administered:

A) orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example maize starch, gelatin or acacia, and lubricating agents, for example magnesium stearate or stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulation for oral use may also be presented as hard gelatin capsules wherein the active ingredient is mixed with an inert solid diluent, for example, calcium carbonate, calcium phosphate or kaolin, or soft gelatin capsules wherein the active ingredient is mixed with water or an oil medium, for example, peanut oil, liquid paraffin or olive oil. Aqueous suspensions contain the active materials in admixture with excipients suitable for the manufacture of aqueous suspensions.

Such excipients are suspending agents, for example, sodium carboxymethylcellulose, methylcellulose, hydroxy, propylmethyl cellulose, sodium alginate, polyvinylpyrrolidone, gum. tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and a hexitol anhydrides, for example polyoxyethylene sorbitan monooleate.

The said aqueous suspensions may also contain one or more preservatives, for example, ethyl or n-propyl phydroxybenzoate, one or more coloring agents, one or more flavoring agents, or one or more sweetening agents, such as sucrose or saccharin. Oily suspension may be formulated by suspending the active ingredient in a vegetable oil, for example arachis oil, olive oil, sesame oil or coconut oil or in a mineral oil such as liquid paraffin. The oily suspensions may contain a thickening agent, for example beeswax, hard paraffin or cetyl alcohol Sweetening agents, such as those set forth above, and flavoring agents may be added to provide a palatable oral preparation.

These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and agents, may also be present.

The pharmaceutical compositions of the invention may also be in the form of oil-in-water emulsions. The oily phase may be a vegetable oil, for example olive oil or arachis oil, or a mineral oil for example liquid paraffin or mixtures of these.

Suitable emulsifying agents may be naturally-occurring gums, for example gum acacia or gum tragacanth, naturallyoccurring phosphatides, for example soy bean, lecithin, and esters or partial esters derived from fatty acids and hexitol anhydrides, for example sorbitan mono-oleate, and condensation products of the said partial esters with ethylene oxide, for example polyoxy ethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents.

B) Parenterally, either subcutaneously or intravenously or intramuscularly, or intrasternally, or by infusion techniques, in the form of sterile injectable aqueous or oleaginous suspension. The pharmaceutical compositions may be in the form of a sterile injectable aqueous or oleaginous suspensions.

This suspension may be formulated according to the known art using those suitable dispersing or wetting agents and suspending agents which have been described above. The sterile injectable preparation may also be a sterile injectable solution or suspension in a non-toxic parenterallyacceptable diluent or solvent for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oils may be conventionally employed including synthetic mono- or diglycerides. In addition fatty acids such as oleic acid find use in the preparation of injectables.

The present invention further provides a method of treating a human or animal, e.g. a mammal, suffering from or susceptible to an amyloidotic disease which method comprises administering thereto a non-toxic and therapeutically effective amount of a compound of the formula 1 or a pharmaceutically acceptable salt thereof.

A typical daily dose is from about 0.1 to about 50 mg per kg of body weight, according to the activity of the specific compound, the age, weight and conditions of the subject to be treated, the type and the severity of the disease, and the frequency and route of administration; preferably, daily dosage levels are in the range of 5 mg to 2 g. The amount of active ingredient that may be combined with the carrier materials to produce a single dosage form will vary depending upon the host treated and the particular mode of administration. For example, a formulation intended for the oral may contain from 5 mg to 2 g of active agent compounded with an appropriate and convenient amount of carrier material which may vary from about 5 to about 95 percent of the total composition. Dosage unit forms will generally contain between from about 5 mg to about 500 mg of the active ingredient. The following examples illustrate the invention without limiting it.

EXAMPLE 1

14-(1,2,3,6-tetrahydropyridin-1-yl)daunomycinone (1a)

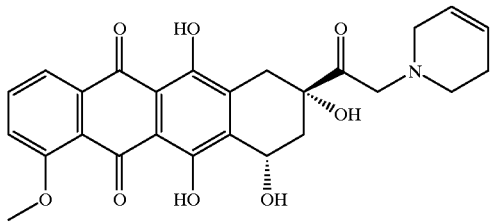

To a suspension of 8.11 g (0.01699 mol) of 14-bromodaunomycinone (prepared as described in T. H. Smith et al., *J. Org. Chem.* 1977, vol. 42, p. 3653) in 510 ml of dichloromethane were added N,N-diisopropylethylamine (3.49 ml, 0.02039 mol.) and 1,2,3,6-tetrahydropyridine (1.85 ml, 0.02039 mol.). The reaction mixture was stirred 6 hours at room temperature. The reaction mixture was then diluted with dichloromethane, washed with water and the organic phase dried over anhydrous sodium sulphate. The solvent was evaporated under reduced pressure and the product was isolated by column chromatography on silica gel with chloroform-methanol 98:2 (by volume) as eluant. The crude product was triturated with diethyl ether, filtered and washed with diethyl ether to give 5.30 g (65% yield) of the title compound 1a, m.p. 177–180° C. (dec.).

ESI-MS, m/z: 480 [M+H]⁺

¹H-NMR (400 MHz, CDCl₃), δ:

2.15 (dd, J=4.7, 14.5 Hz, 1H, H-8ax); 2.26 (m, 2H, CH₂-3 tetrahydropyridine); 2.37 (ddd, J=2.1, 2.1, 14.5 Hz, 1H, H-8eq); 2.73 (m, 2H, CH₂-2 tetrahydropyridine); 2.97 (d, J=18.4 Hz, 1H, H-10ax); 3.15 (m, 2H, CH₂-6 tetrahydropyridine); 3.19 (dd, J=2.1, 18.4 Hz, 1H, H-10eq); 3.61, 3.78 (two doublets, J=15.8 Hz, 2H, CH₂-14); 4.07 (s, 3H, OCH₃); 5.25 (dd, J=2.1, 4.7 Hz, 1H, H-7); 5.65, 5.80 (two multiplets, 2H, CH=CH tetrahydropyridine); 7.38 (dd, J=0.8, 8.5 Hz, 1H, H-3); 7.76 (dd, J=7.7, 8.5 Hz, 1H, H-2); 8.02 (dd, J=0.8, 7.7 Hz, 1H, H-1); 13.30, 13.97 (broad signals, 2H, OH-6+OH-11).

The compound 1a was transformed into its hydrochloride salt according to the following procedure. A solution of 1.08 g of 1a in 20 ml of dichloromethane was treated, under stirring, with 1.25 ml of 2N HCl in isopropanol. Diethyl ether was then added dropwise and stirring was continued for 15 minutes. The precipitated salt was filtered, washed extensively with diethyl ether and dried under vacuum at 30° C. to give 1.13 g of a red solid, m.p. 188–190° C. (dec.).

EXAMPLE 2

13-dihydro-14-(1,2,3,6-tetrahydropyridin-1-yl)daunomycinone (1b)

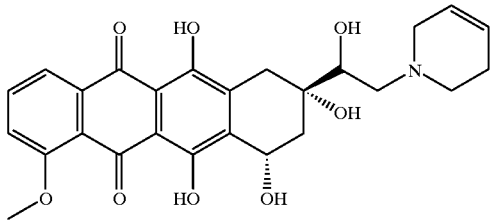

To a solution of compound 1a (1.8 g, 0.00375 mol.) in 36 ml of methanol were added 36 ml of a methanolic solution of acetic acid (prepared by diluting 3 ml of glacial acetic acid to 50 ml with methanol) and a solution of sodium cyanoborohydride (1.17 g, 0.01876 mol.) in 18 ml of methanol. The reaction mixture was stirred 3 hours at room temperature. A second portion of sodium cyanoborohydride (0.6 g, 0.00938 mol.) was added and the reaction mixture was stirred 2 hours; after that period a third portion of sodium cyanoborohydride (0.3 g, 0.00469 mol.) was added and the reaction stirred for an additional hour. The reaction mixture was poured onto 8.82 g of sodium hydrogen carbonate and the solvent was evaporated under reduced pressure. The residue was taken up with 1 L of water and extracted with dichloromethane. The organic extracts were combined, dried over anhydrous sodium sulphate and evaporated under reduced pressure. The residue was triturated with diethyl ether and filtered to give 1.52 g of crude 1b. An amount of the crude product (0.3 g) was purified by column chromatography on silica gel, using a mixture of chloroform and methanol (47:3 by volume) as eluant, to give 0.13 g of pure 1b as a mixture of diastereoisomers, m.p. 105–107° C. (dec.).

ESI-MS, m/z: 482 [M+H]⁺

¹H-NMR (400 MHz, DMSO-d₆), δ:

1.80 (dd, J=4.4, 14.4 Hz, 1H, H-8ax); 1.96 (m, 2H, CH₂-8, second diastereoisomer); 2.09 (m, 2H, CH₂-3 tetrahydropyridine, both distereoisomers); 2.10 (m, 1H, H-8eq); 2.5–3.0 (m, 8H, CH₂-10+CH₂-14+CH₂-2 and CH₂-6 tetrahydropyridine of both distereoisomers); 3 56 (dd, J=4.7, 76 Hz, 1H, CH-13); 3.6 (dd, J=5.6 Hz, 1H, CH-13 second diastereoisomer); 3 96 (s, 3H, OCH₃ both diastereoisomers); 4.99 (m, 1H, H-7 both diastereoisomers); 5.65 (m, 2H, CH=CH tetrahydropyridine); 7.61 (m, 1H, H-3); 7.86 (m, 2H, H-1+H-2); OH-6 and OH-11 not seen. Operating as described in example 1, the title compound is transformed into its hydrochloride salt, m.p. 175–177° C. (dec.).

EXAMPLE 3

(13S)-7-deoxy-13-dihydro-14-(1,2,3,6-tetrahydropyridin-1-yl)daunomycinone (1c) and (13R)-7-deoxy-13-dihydro-14-(1,2,3,6-tetrahydropyridin-1-yl)daunomycinone (1d)

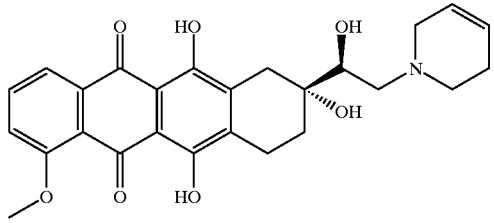

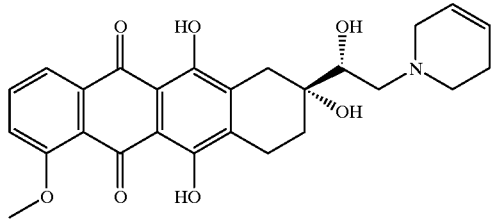

To a solution of 1b (5.9 g, 0.01225 mol.) in 100 ml of dimethylformamide, under nitrogen, was added dropwise, under stirring, sodium dithionite (6.26 g, 0.0306 mol.) in 50 ml of water. The reaction mixture was stirred 2 hours at room temperature, poured into 1.5 L of water and extracted with chloroform. The organic phase was washed with brine, dried over anhydrous sodium sulphate and evaporated under reduced pressure. The residue was separated by column chromatography on silica gel, using a mixture of chloroform and methanol (47:3 by volume) as the eluant. Upon a first chromatography, a pure fraction of 0.69 g of the less polar isomer 1c was obtained, m.p. 215–218° C. (dec.).

ESI-MS, m/z: 466 [M+H]⁺

¹H-NMR (400 MHz, CDCl₃), δ:

1.60 (m, 1H, H-8ax); 2.20 (m, 2H, CH₂-3 tetrahydropyridine); 2.28 (m, 1H, H-8eq); 2.58, 2.85 (m, 2H, CH₂-10); 2.60, 2.85 (m, 2H, CH₂-2 tetrahydropyridine); 2.67, 2.85 (m, 2H, CH₂-14); 2.85, 3.00 (m, 2H, CH₂-7); 3.00, 3.22 (m, 2H, CH₂-6 tetrahydropyridine); 3.66 (dd, J=3.8, 9.8 Hz, 1H, CH-13); 4.07 (s, 3H, OCH); 5.65, 5.75 (two multiplets, 2H, CH=CH tetrahydropyridine); 7.35 (d, J=8.6 Hz, 1H, H-3); 7.74 (dd, J=7.7, 8.6 Hz, 1H, H-2); 8.02 (d, J=7.7 Hz, 1H, H-1); 13.55, 13.87 (two singlets, 2H, OH-6+OH-11).

Operating as described in example 1, the title compound was transformed into its hydrochloride salt, m.p. 248–251° C. (dec.)

The fractions rich in the other isomer were combined and separated by column chromatography to give a pure fraction of 0.1 g of the more polar isomer 1d, m.p. 194–196° C. (dec.).

ESI-MS, m/z: 466 [M+H⁺

¹H-NMR (400 MHz, CDCl₃), δ:

1.70 (m, 2H, H-8ax); 1.92 (m, 1H, H-8eq); 2.18 (m, 2H, CH₂-3 tetrahydropyridine); 2.6-2.8 (m, 4H, CH₂-2 tetrahydropyridine +CH₂-14); 2.9, 3.2 (m, 6H, CH₂-10+CH₂-7+ CH₂-6 tetrahydro-pyridine); 3.74 (dd, J=5.1, 9.0 Hz, 1H, CH-13); 4.08 (s, 3H, OCH₃); 5.65, 5.75 (two multiplets, 2H, CH=CH tetrahydro-pyridine); 7.36 (d, J=7.7 Hz, 1H, H-3); 7.75 (dd, J=7.7, 7.7 Hz, 1H, H-2); 8.04 (d, J=7.7 Hz, 1H, H-1); 13.52, 13.90 (two singlets, 2H, OH-6+OH-11)

Operating as described in example 1, the title compound is transformed into its hydrochloride salt, m.p. >270° C.

EXAMPLE 4

(13S)-7-deoxy-13-dihydro-14-(1,2,3,6-tetrahydropyridin-1-yl)daunomycinone 9,13-isopropylidenketal (1e)

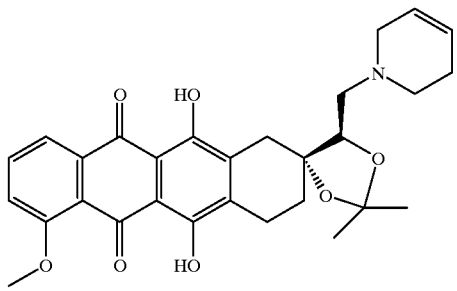

To a solution of 1c (0.24 g, 0.00051 mol.) in 9 ml of anhydrous dimethylformamide were added 25 ml of 2,2dimethoxypropane and 0.8 ml of trifluoromethanesulfonic acid. The reaction was heated at 900C for 3 hours, then a second portion of 2,2-dimethoxypropane (10 ml) and trifluoromethanesulfonic acid (0.4 ml) were added and the reaction heated for additional two hours. The reaction mixture was poured into 500 ml of a saturated sodium hydrogen carbonate solution and extracted with ethyl acetate. The organic phase was washed with water, dried over anhydrous sodium sulphate and evaporated under reduced pressure. The residue was chromatographed on silica gel, using a mixture of chloroform and methanol (50:1 by volume) as eluant, to give 0.14 g (53% yield) of the title compound le, m.p. 183-185° C. (dec.).

ESI-MS, m/z: 506 [M+H]⁺

¹H-NMR (400 MHz, CDCl₃), δ:

1.38, 1.42 (two singlets, 6H, C(CH₃)₂); 1.90 (m, 2H, CH₂-8); 2.14 (m, 2H, CH₂-3 tetrahydropyridine); 2.51, 2.75 (m, 2H, CH₂-2 tetrahydropyridine); 2.62, 2.75 (m, 2H, CH₂-14); 2.70, 3.00 (m, 2H, CH₂-10); 2.9-3.2 (m, 4H, CH₂-7+CH₂-6 tetra-hydropyridine); 4.07 (s, 3H, OH); 4.15 (dd, J=4.7, 6.8 Hz, 1H, CH-13); 5.60, 5.70 (two multiplets, 2H, CH=CH tetrahydro-pyridine); 7.35 (d, J=8.6 Hz, 1H, H-3); 7.74 (dd, J=7.7, 8.6 Hz, 1H, H-2); 8.03 (d, J=7.7 Hz, 1H, H-1); 13.54, 13.85 (two singlets, 2H, OH-6+OH-11).

EXAMPLE 5

(13R)-7-deoxy-13-dihydro-14-(1,2,3,6-tetrahydropyridin-1-yl)daunomycinone 9,13-isopropylidenketal (1f)

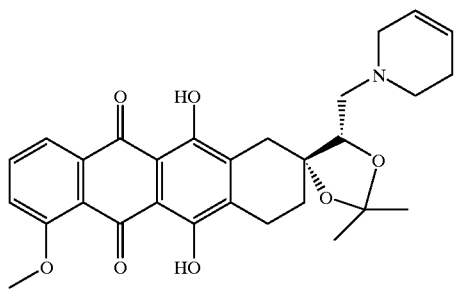

Starting from compound 1d, and operating as described in example 4, the title compound if was obtained in 45% yield, m.p. 133–135° C. (dec.).

ESI-MS, m/z: 506 [M+H]⁺

¹H-NMR (400 MHz, CDCl₃), δ:

1.39, 1.46 (two singlets, 6H, C(CH₃)₂); 1.50 (m, 1H, CH(H)-8); 2.05 (m, 1H, CH(H)-8); 2.18 (m, 2H, CH₂-3 tetrahydropyridine); 2.5–3.2 (m, 8H, CH₂-14+CH₂-2 tetrahydropyridine+CH₂-6 tetrahydropyridine+CH₂-7); 2.90 (m, 2H, CH₂-10); 4.07 (s, 3H, OCH ); 4.24 (dd, J=4.7, 7.3 Hz, 1H, CH-13); 5.65, 5.72 (two multiplets, 2H, CH=CH tetrahydropyridine); 7.35 (d, J=8.1 Hz, 1H, H-3); 7.74 (dd, J=7.7, 8.1 Hz, 1H, H-2); 8.03 (d, J=7.7 Hz, 1H, H-1); 13.50, 13.88 (two singlets, 2E, OH-6+OH-11).

EXAMPLE 6

7-deoxy-14-(1,2,3,6-tetrahydropyridin-1-yl) daunomycinone (1g)

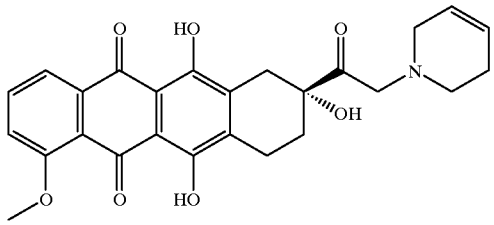

To a solution of 1a (0.5 g, 0.001 mol.) in 8 ml of dimethylformamide, under nitrogen, was added dropwise, under stirring, sodium dithionite (0.53 g, 0.026 mol.) in 4 ml of water. The reaction mixture was stirred 3 hours at room temperature, poured into 100 ml of water and extracted with chloroform. The organic phase was washed with brine, dried over anhydrous sodium sulphate and evaporated under reduced pressure. The residue was separated by column chromatography on silica gel, using a mixture of chloroform and methanol (48:2 by volume) as the eluant, to give 0.21 g (43% yield) of the title compound ig, m.p. 196–198° C. (dec.).

ESI-MS, m/z: 464 [M+H]⁺

¹H-NMR (400 MHz, CDCl₃), δ:

2.00 (m, 2H, CH₂-8); 2.25 (m, 2H, -3 tetrahydropyridine); 2.75 (m, 2H, CH₂-2 tetrahydropyridine); 2.9-3.1 (m, 2H, CH₂-7); 3.05 (m, 2H, CH₂-10); 3.18 (m, 2H, CH₂-6 tetrahydropyridine); 3.53, 3.68 (two doublets, J=14.5 Hz, 2H, CH₂-14); 4.08 (s, 3H, OCH₃); 5.65, 5.80 (two multiplets, 2H, CH=CH tetrahydropyridine); 7.36 (d, J=8.5 Hz, 1H, H-3); 7.75 (dd, J=77, 8.5 Hz, 1H, H-2); 8.03 (d, J=7.7 Hz, 1H, H-1); 13.48, 13.86 (two singlets, 2H, OH-6+OH-11).

Operating as described in example 1, the title compound is transformed into its hydrochloride salt.

EXAMPLE 7

4-demethyl-14-(1,2,3,6-tetrahydrooyridin-1-yl) daunomycinone (1h)

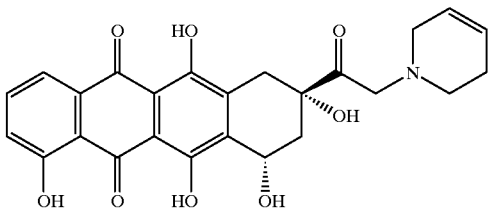

The title compound was prepared as described in example 1 starting from 4-demethyl-14-bromodaunomycinone which was obtained by bromination, according to a literature procedure (see: T. H. Smith et al., *J. Org. Chem.* 1977, vol. 42, p. 36533, of 4-demethyldaunomycinone. 4-demethyldaunomycinone was prepared as described in G. Cassinelli et al. *J. Antibiotics* 1978, vol 31, p. 178.

ESI-MS, m/z: 466 [M+H]$^+$ $^1$H-NMR (400 MHz, DMSO-d$_6$), δ:

2.0–2.2 (m, 2H, CH-8); 2.08 (m, 2H, CH -3 tetrahydropyridine); 2.57 (m, 2H, CH$_2$-2 tetrahydropyridine); 2.9–3.1 (m, 4H, CH$_2$-10+CH$_2$-6 tetrahydropyridine); 3.75, 3.81 (two doublets, J=18.8 Hz, 2H, CH$_2$-14); 5.04 (m, 1H, H-7); 5.61, 5.68 (two multiplets, 2H, CH=CH tetrahydropyridine); 6.10 (broad signal, 2H, OH-7+OH-9); 7.39 (m, 1H, H-3); 7.80 (m, 2H, H-1+H-2); 11.9, 12.8 (broad signals, 2H, OH-11+OH-4); 13.40 (broad signal, 1H, OH-6).

Operating as described in example 1, the title compound is transformed into its hydrochloride salt.

EXAMPLE 8

(9S)-4-demethoxy-7-deoxy-14-(1,2,3,6-tetrahydropyridin-1-yl)daunomycinone (1i)

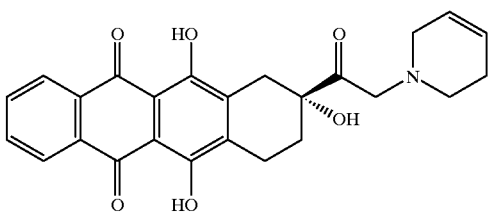

The title compound was prepared as described in example 1 starting from (95S)-4-demethoxy-7-deoxy-14-bromodaunomycinone which was obtained by bromination, according to a literature procedure (see: T. H. Smith et al., *J. Org. Chem.* 1977, vol. 42, p. 3653), of (9S)-4-demethoxy-7-deoxy-daunomycinone. The title compound has m.p. 150–153° C. (dec.).

ESI-MS, m/z: 434 [M+H]$^+$ $^1$H-NMR (400 MHz, CDCl$_3$), δ:

2.00 (m, 2H, CH$_2$-8); 2.25 (m, 2H, CH$_2$-3 tetrahydropyridine); 2.74 (m, 2H, 2C2-2 tetrahydropyridine); 2.9-3.1 (m, 2H, CH$_2$-7); 3.03 (m, 2H, CH$_2$-10); 3.15 (m, 2H, CH$_2$-6 tetrahydropyridine); 3.49, 3.65 (two doublets, J-14.6 Hz, 2H, CH$_2$-14) 5.65, 5.80 (two multiplets, 2H, CH=CH tetrahydropyridine); 7.80 (m, 2H, H-2+H-3); 8.33 (m, 2H, H-1+H-4); 13.48 (s, 2H, OH-6+ OH-11).

Operating as described in example 1, the title compound is transformed into its hydrochloride salt.

EXAMPLE 9

(9R)-4-demethoxy-7-deoxy-14-(1,2,3,6-tetrahydroyridin-1-yl)daunomycinone (1j)

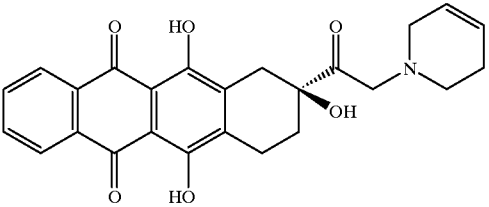

The title compound was prepared as described in example 1 starting from (9R)-4-demethoxy-7-deoxy-14-bromodaunomycinone which was obtained by bromination, according to a literature procedure (see: T. H. Smith et al., *J. Org. Chem.* 1977, vol. 42, p. 3653), of (9R)-4-demethoxy-7-deoxy-daunomycinone. The starting material (9R)-4-demethoxy-7-deoxy-daunomycinone was obtained following the procedure described in C. M. Wong et al. *Can. J. Chem.* 1971, vol.49, p. 2712.

ESI-MS, m/z: 434 [M+H]$^+$ $^1$H-NMR (200 MHz, CDCl$_3$), δ:

2.00 (m, 2H, CH$_2$-8); 2.25 (m, 2H, CH$_2$-3 tetrahydropyridine); 2.74 (m, 2H, CH$_2$-2 tetrahydropyridine); 2.9-3.1 (m, 2H, CH$_2$-7); 3.03 (m, 2H, CH$_2$-10); 3.15 (m, 2H, CH$_2$-6 tetrahydropyridine); 3.49, 3.65 (two doublets, J=14.6 Hz, 2H, CH$_2$-14); 5.65, 5.80 (two multiplets, 2H, CH=CH tetrahydropyridine); 7.80 (m, 2H, H-2+H-3); 8.33 (m, 2H, H-1+H-4); 13.48 (s, 2H, OH-6+ OH-11).

Operating as described in example 1, the title compound is transformed into its hydrochloride salt.

EXAMPLE 10

7-deoxy-7-(4-morpholinyl) -14-(1,2,3,6-tetrahydropyridin-1-yl)daunomycinone (1k)

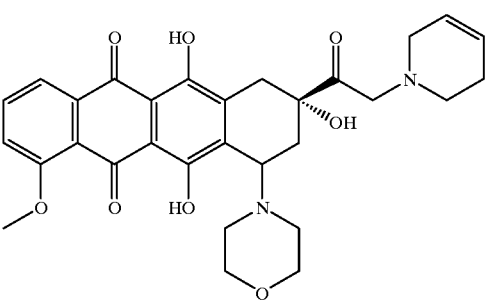

To a solution of compound 1a (1 g, 0.00208 mol.) and triethylamine (3 ml, 0.0208 mol) in 65 ml of dichloromethane was added dropwise, under stirring and cooling to 0° C. with an ice bath, ethyl chlorocarbonate (1.52 ml, 0.01589 mol.) in 10 ml of dichloromethane. The reaction mixture was stirred 2 hours at room temperature then was diluted with dichloromethane, washed with water and dried over anhydrous sodium sulphate The resulting solution was evaporated under reduced pressure to give 1.65 g of a yellow residue of crude 6,7,11-triethoxycarbonyl-14-(1,2,3,6-tetrahydropyridin-1yl)daunomycinone which was used as such in the next step. The crude 6,7,11-triethoxycarbonyl-14-(1,2,3,6-tetrahydropyridin-1-yl)daunomycinone was stirred 15 minutes in 10 ml of morpholine. The reaction mixture was diluted with chloroform and washed with water and then with a pH 7 buffer. The organic phase was dried on anhydrous sodium sulphate, evaporated under reduced pressure and the product was isolated by column chromatography on silica gel, using a mixture of chloroform and methanol (48:2 by volume) as the eluant. The title compound 1k (0.28 g) was obtained in 24% overall yield, m.p. 137–138° C.

ESI-MS, m/z: 549 (M+H]$^+$ $^1$H-NMR (400 MHz, CDCl$_3$), δ:

1.83 (dd, J=3.4, 14.5 Hz, 1H, CH(H)-8); 2.25 (m, 2H, CH2-3 tetrahydropyridine); 2.36 (dd, J=2.6, 14.5 Hz, 1H, CH(H)-8); 2.50, 3.00 (two multiplets, 4H, N(CH$_2$)$_2$(CH$_2$)$_2$O); 2.70 (m, 2H, CH$_2$-2 tetrahydropyridine); 3.15 (m, 2H, CH$_2$-6 tetrahydro-pyridine); 319 (s, 2H, CH$_2$-10); 3.65 (m, 4H, N(CH$_2$)$_2$(CH$_2$)$_2$O); 3.82, 3.99 (two doublets, J=19.4 Hz, 2H, CH$_2$-14); 4.09 (s, 3H, OCH$_3$); 4.35 (dd, J=2.6, 3.4 Hz, 1H, H-7); 5.65, 5.78 (two multiplets, 2H, CH═CH tetrahydropyridine); 7.40 (d, J=7.7 Hz, 1H, H-3); 7.79 (dd, J=7.7 Hz, 1H, H-2); 8.04 (d, J=7.7 Hz, 1H, H-1); 13.30, 14.12 (broad signals, 2H, OH-6+OH-11).

Operating as described in example 1, the title compound is transformed into its hydrochloride salt.

EXAMPLE 11

Tablets containing the following ingredients may be produced in a conventional manner:

| Ingredient | Per Tablet |
| --- | --- |
| Compound 1 | 25.0 mg |
| Lactose | 125.0 mg |
| Maize starch | 75.0 mg |
| Talc | 4.0 mg |
| Magnesium stearate | 1.0 mg |
| Total weight | 230.0 mg |

EXAMPLE 12

Capsules containing the following ingredients may be produced in a conventional manner:

| Ingredient | Per capsule |
| --- | --- |
| Compound 1 | 50.0 mg |
| Lactose | 165.0 mg |
| Maize starch | 20.0 mg |
| Talc | 5.0 mg |
| Capsule weight | 240.0 mg |

What is claimed is:

1. A compound of formula 1

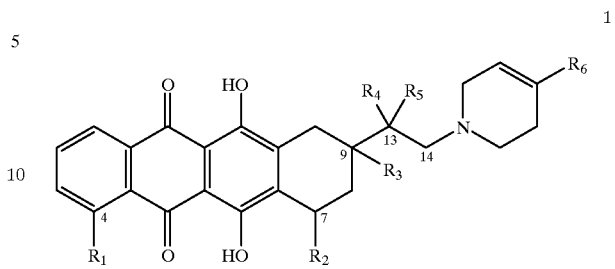

wherein R, represents:
hydrogen,
hydroxy,
a group of formula OR$_7$ wherein R$_7$ is C$_1$–C$_6$ alkyl, C$_2$–C$_6$ alkenyl;

R$_2$ represents:
hydrogen,
hydroxy,
diethylamino, piperidino, tetrahydropyridino or morpholino;

and either R$_3$, taken alone, represents hydrogen or hydroxy, and R$_4$ and R$_5$, when taken alone, independently represent hydrogen, hydroxy or, taken together with the carbon atom, represent a carbonyl group;

or R$_3$ and R$_4$, taken together, represent a group of formula

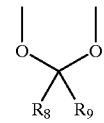

wherein R$_8$ and R$_9$ represent a C$_1$–C$_6$ alkyl and R$_5$ represents hydrogen;

R$_6$ represents:
hydrogen or
a phenyl group, optionally substituted by methyl, methoxy or halogen,
and the pharmaceutically acceptable salt thereof.

2. A compound according to claim 1, characterized in that
R$_1$ represents:
hydrogen,
hydroxy or methoxy;
R$_2$ represents:
hydrogen,
hydroxy or
morpholino
R$_3$ represents hydroxy;
R$_4$, taken alone, represents hydroxy;
R$_5$, taken alone, represents hydrogen or
R$_4$ and R$_5$ taken together with the carbon atom represent a carbonyl group;
R$_6$ represents hydrogen, and the pharmaceutically acceptable salt thereof.

3. A compound according to claim 1, which is 14-(1,2,3,6-tetrahydropyridin-1-yl)daunomycinone, or a pharmaceutically acceptable salt thereof.

4. A process for preparing a compound of formula 1, as defined in claim 1, which process comprises:

(a) reacting a compound of formula 2,

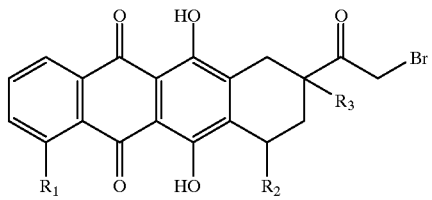

wherein $R_1$, and $R_3$ are as defined in claim 1 and $R_2$ is hydrogen or hydroxy, with a compound of formula 3

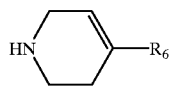

wherein $R_6$ is as defined in claim 1, and
(b) converting a compound of formula 1 as defined above into a different compound of formula 1 by appropriate chemical reactions, and/or if desired, converting the resulting compound of formula 1 into a pharmaceutically acceptable salt thereof.

5. A process according to claim 4, wherein in step (a) a compound of formula 2 as defined in claim 4 is reacted with a compound of formula 3 as defined in claim 4 in a proper organic solvent at a temperature ranging from −10° C. to room temperature and for a period of from 6 to 48 hours.

6. A pharmaceutical composition which comprises, as active ingredient, a compound of formula 1 as defined in claim 1, or a pharmaceutically acceptable salt thereof, in admixture with a pharmaceutically acceptable carrier or diluent.

7. A compound of formula 1 as defined in claim 1, or a pharmaceutically acceptable salt thereof, for use in the treatment of the human or animal body.

8. A method of treating a human or animal suffering from, or susceptible to, an amyloidois disease, which method comprises administering thereto a non-toxic and effective amount of a compound of formula (I), as defined in claim 1, or a pharmaceutically acceptable salt thereof.

* * * * *